(12) United States Patent
Melson et al.

(10) Patent No.: US 8,268,069 B2
(45) Date of Patent: Sep. 18, 2012

(54) PEARLESCENT PIGMENTS

(75) Inventors: Sabine Melson, Mainz (DE); Marc Entenmann, Fellbach (DE); Marita Jekel, Darmstadt (DE); Marcus Mathias, Gernsheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 11/659,954

(22) PCT Filed: Aug. 10, 2005

(86) PCT No.: PCT/EP2005/008658
§ 371 (c)(1),
(2), (4) Date: Sep. 20, 2007

(87) PCT Pub. No.: WO2006/018196
PCT Pub. Date: Feb. 23, 2006

(65) Prior Publication Data
US 2008/0168924 A1    Jul. 17, 2008

(30) Foreign Application Priority Data
Aug. 13, 2004   (DE) .......... 10 2004 039 554

(51) Int. Cl.
*C09C 1/00*   (2006.01)
*C09C 3/06*   (2006.01)

(52) U.S. Cl. ........ 106/442; 106/415; 106/436; 106/446; 106/483; 106/484; 106/489; 106/490; 427/218; 427/219; 428/403; 428/404

(58) Field of Classification Search .................. 106/436, 106/438, 442, 446, 415, 483, 484, 489, 490; 427/218, 219; 428/403, 404
See application file for complete search history.

(56) References Cited

U.S. PATENT DOCUMENTS

| | | |
|---|---|---|
| 2,232,168 A | 2/1941 | Dawson |
| 4,482,389 A | 11/1984 | Franz et al. |
| 5,376,698 A | 12/1994 | Sipsas |
| 5,472,491 A | 12/1995 | Duschek et al. |
| 6,488,758 B2 | 12/2002 | Glausch et al. |
| 7,226,503 B2 * | 6/2007 | Anselmann et al. .......... 106/489 |
| 2004/0003758 A1 | 1/2004 | Bruckner et al. |
| 2004/0170838 A1 | 9/2004 | Ambrosius |
| 2006/0051304 A1 * | 3/2006 | Peng et al. ..................... 424/59 |
| 2006/0225609 A1 | 10/2006 | Rueger et al. |

FOREIGN PATENT DOCUMENTS

| | | |
|---|---|---|
| CA | 2 238 035 | 3/1998 |
| DE | 32 35 017 | 3/1984 |
| DE | 196 38 708 | 4/1998 |
| EP | 0 632 109 | 1/1995 |
| EP | 0 644 242 A | 3/1995 |
| EP | 1 203 794 | 5/2002 |
| WO | WO02/090448 A2 * | 11/2002 |
| WO | WO 03/006558 A | 1/2003 |
| WO | WO 2004/055119 A | 7/2004 |
| WO | WO-2004 092284 | 10/2004 |

OTHER PUBLICATIONS

Extract from the Register of European Patents for EP-1 611 209, Publication Date: Oct. 26, 2004.
Glausch, R. et al., Perlglanzpigmente, Die Technologie des Beschichtens, 1996, pp. 16-17.
Pfaff, G., "Special Effect Pigments," European Coatings Tech Files, Apr. 2008, pp. 74-76.

* cited by examiner

*Primary Examiner* — Anthony J Green
(74) *Attorney, Agent, or Firm* — Millen, White, Zelano & Branigan, P.C.

(57) ABSTRACT

The present invention relates to pearlescent pigments based on glass flakes which are distinguished by the fact that they have the following layer structure: A) optionally a layer of $SiO_2$, B) a high-refractive-index coating have a refractive-index n>1.8 which essentially consists of $TiO_2$, C) a low-refractive-index layer comprising $SiO_2$ and/or $Al_2O_3$ and optionally D) an outer protective layer, and to the use thereof in paints, coatings, automobile paints, powder coatings, printing inks, security printing inks, plastics, ceramic materials, glasses, paper, in toners for electrophotographic printing processes, in seed, in greenhouse sheeting and tarpaulins, as absorbers in the laser marking of paper and plastics, as absorbers for the laser welding of plastics, in cosmetic formulations, for the preparation of pigment pastes with water, organic and/or aqueous solvents, for the preparation of pigment compositions and dry preparations.

13 Claims, No Drawings

PEARLESCENT PIGMENTS

The present invention relates to pearlescent pigments based on multi-coated glass flakes and to the use thereof, inter alia in paints, coatings, printing inks, plastics and in cosmetic formulations. The pigments according to the invention are particularly suitable for the pigmenting of plastics since they have increased chemical and mechanical stability.

Silver-white pigments are employed as lustre or effect pigments in many areas of industry, in particular in decorative coatings, in plastics, in paints, coatings, printing inks and in cosmetic formulations.

Plastics are used indoors and outdoors and generally comprise a number of additives in order to improve the properties, such as, for example, plasticisers, fillers, stabilisers and anti-ageing agents, lubricants and release agents, antistatics and colorants. For decorative purposes, pigments, in particular silver-white pigments, or effect pigments are added to the plastics. An undesired interaction is frequently observed, in particular, between the pigments on the one hand and stabilisers and antiageing agents on the other hand which presumably consists in the stabiliser and/or antiageing agent molecules diffusing to the surface of the pigment particles, where they cause a yellowing reaction, which often also proceeds in the dark, in particular if the plastics comprise phenolic components as antioxidants, thermal stabilisers or UV stabilisers.

Plastics having phenolic constituents exhibit yellowing from a pigment concentration as low as 0.01% by weight. In particular if sterically readily accessible phenol compounds are present in the plastic, the yellowing reaction may already be evident during processing. In the case of sterically poorly accessible compounds, by contrast, the yellowing sometimes only occurs 18 months after processing. In general, the yellowing reaction is visible with the eye within 2 h in the case of processing at 80° C. and at a pigment concentration of, for example, 0.1% by weight. The yellowing reaction leads to unattractive effects, in particular, in the case of pigments having a pale hue and considerably impairs the aesthetic impression of the plastic system. The cause of the yellowing reaction is frequently the photo-activity of the titanium dioxide layer of effect pigments; which considerably accelerates the photolytic decomposition of the organic constituents in the plastic or coating.

A further problem in plastics is pigmentation by effect pigments based on flake-form substrates, since the pigments are subject to very considerable stressing on incorporation into the plastic. The stressing may become so great that the pigments break and the optical effect is consequently modified. The larger the flakes, the greater the probability that the flake shape is destroyed on incorporation into the plastic. In particular, effect pigments having an aspect ratio (diameter/flake thickness) of >50, very particularly preferably of >100, frequently cause problems on incorporation.

The object of the present invention is to provide pearlescent pigments, in particular interference pigments and silver-white pigments, having high lustre and bright interference colours which have increased mechanical stability and at the same time have high storage stability in polymers, in particular in phenol-containing plastics and coatings.

Surprisingly, it has now been found that pearlescent pigments based on glass flakes which exhibit a certain layer structure and have a calcined $SiO_2$ and/or $Al_2O_3$ layer as outer layer have significantly higher mechanical and chemical stability on incorporation into polymers, in particular plastics, than, for example, silver-white pigments based on mica flakes.

The present invention therefore relates to pearlescent pigments based on glass flakes which are distinguished by the fact that they have the following layer structure:
  (A) optionally a layer of $SiO_2$,
  (B) a high-refractive-index coating having a refractive index n>1.8 which essentially consists of $TiO_2$,
  (C) a low-refractive-index layer comprising $SiO_2$ and/or $Al_2O_3$
and optionally
  (D) an outer protective layer.

The pigments according to the invention are distinguished not only by their optical effects, but also exhibit significantly improved storage stability in polymers, in particular in phenol-containing plastics and coatings. The pigments are furthermore distinguished by increased mechanical stability. Compared with silver-white pigments based on mica flakes, no or only slight pale/dark yellowing is observed in the plastic, i.e. the pigments according to the invention exhibit no or only a slight surface reaction with the plastic.

The invention furthermore relates to the use of the pearlescent pigments according to the invention in paints, coatings, in particular automobile paints, powder coatings, printing inks, security printing inks, plastics, ceramic materials, glasses, paper, in toners for electrophotographic printing processes, in seed, in greenhouse sheeting and tarpaulins, as absorbers in the laser marking of paper and plastics, as absorbers in the laser welding of plastics and in cosmetic formulations. The pigments according to the invention are furthermore also suitable for the preparation of pigment pastes with water, organic and/or aqueous solvents, pigment compositions and for the preparation of dry preparations, such as, for example, granules, chips, pellets, briquettes, etc. The dry preparations are particularly suitable for printing inks and in cosmetics.

Suitable base substrates are glass flakes owing to their smooth surfaces and their very high reflection capacity. The size of the base substrates is not crucial per se and can be matched to the particular application. Particular preference is given to glass flakes having an average thickness of <2 μm. Thicker flakes generally cannot be employed in common printing processes and in demanding paint finishes. The glass flakes preferably have thicknesses of <1 μm, in particular of <0.9 μm, very particularly preferably of <0.7 μm. Particular preference is given to glass flakes having thicknesses of 0.25-0.7 μm. The diameter of the glass flakes is preferably 5-300 μm, particularly preferably 10-100 μm, furthermore 5-60 μm. Glass flakes having these dimensions can be prepared, for example, by the process described in EP 0 289 240.

The glass flakes can consist of all glass types known to the person skilled in the art, such as, for example, window glass, C glass, E glass, ECR glass, Duran® glass, laboratory equipment glass or optical glass. Particular preference is given to E glass or ECR glass. The refractive index of the glass flakes is preferably 1.45-1.80, in particular 1.50-1.70.

However, the chemical composition of the glass flakes in the case of coating with an $SiO_2$ layer (layer (A)) is of secondary importance for the further coatings and the resultant applicational properties of the pigments. The $SiO_2$ coating protects the glass surface against chemical modification, such as swelling, leaching-out of glass constituents or dissolution in the aggressive acidic coating solutions.

High-refractive-index coatings are taken to mean layers having a refractive index of >1.8, low-refractive-index layers are taken to mean those having n≦1.8.

The thickness of layer (A) on the substrate can be varied in broad ranges depending on the desired effect. Layer (A) has thicknesses of 2-350 nm, preferably of 5-200 nm. Layer thicknesses of 20-150 nm are preferred for control of lustre and tinting strength.

Layer (B) is preferably a $TiO_2$ layer which may be either in the rutile or in the anatase modification, preferably a rutile layer. However, the $TiO_2$ layer may also be doped with carbon black and/or organic or inorganic colorants, where the proportion of doping should not exceed 10% by weight, based on the $TiO_2$ layer. Rutile is preferably prepared by the process from EP 0 271 767. The thickness of the high-refractive-index $TiO_2$ layer (B) depends on the desired interference colour and on the thickness of the glass flakes. The thickness of layer (B) is preferably 20-300 nm, preferably 30-150 nm and in particular 40-100 nm. Combination of the thin $SiO_2$ layer, if present, with a high-refractive-index metal-oxide layer enables, for example, interference colours from pure silver-white via gold to intense green to be obtained.

If layer (B) is a layer which essentially consists of rutile, full-area or partial coating with $SnO_2$ or partial coating with $SnO_2$ nuclei is preferably carried out before the coating with $TiO_2$. This very thin $SnO_2$ layer has maximum thicknesses of 10 nm, preferably $\leq$5 nm.

The low-refractive-index coating (C) preferably consists of one or more low-refractive-index oxides, in particular of $SiO_2$ and/or $Al_2O_3$, preferably of $SiO_2$. In the case of a mixture of $SiO_2$ and $Al_2O_3$, the mixing ratio is 1:100 to 100:1, preferably 1:50 to 50:1, in particular 1:10 to 10:1. Layer (C) can comprise 0.005-10% by weight, preferably 0.01-8% by weight, in particular 0.05-5% by weight, of further oxides from the group V, Zr, Zn, Ce, Ti, B, Na, K, Mg, Ca and/or Mn. Of the said oxides, particular preference is given to the oxides of V, Zr, Ce and/or Zn. The thickness of the final layer (C) is 2-200 nm, preferably 10-80 nm, in particular 10-60 nm.

Particularly preferred pearlescent pigments are mentioned below:

glass flake+$SiO_2$+$TiO_2$+$SiO_2$ glass flake+$SiO_2$+$TiO_2$+$SiO_2$/$Al_2O_3$ glass flake+$SiO_2$+$TiO_2$+$Al_2O_3$ glass flake+$TiO_2$+$SiO_2$ glass flake+$TiO_2$+$SiO_2$/$Al_2O_3$ glass flake+$TiO_2$+$Al_2O_3$ The pearlescent pigments according td the invention can generally be prepared relatively easily.

The metal-oxide layers are preferably applied by wet-chemical methods, it being possible to use the wet-chemical coating methods developed for the preparation of pearlescent pigments. Methods of this type are described, for example, in DE 14 67 468, DE 19 59 988, DE 20 09 566, DE 22 14 545, DE 22 15 191, DE 22 44 298, DE 23 13 331, DE 15 22 572, DE 31 37 808, DE 31 37 809, DE 31 51 343, DE 31 51 354, DE 31 51 355, DE 32 11 602, DE 32 35 017 and in further patent documents and other publications known to the person skilled in the art.

In the case of wet coating, the substrate particles are suspended in water, and one or more hydrolysable metal salts or a water-glass solution are/is added at a pH which is suitable for hydrolysis and which is selected in such a way that the metal oxides or metal oxide hydrates are precipitated directly onto the flakes without secondary precipitations occurring. The pH is usually kept constant by simultaneous metered addition of a base and/or acid. The pigments are subsequently separated off, washed and dried at 50-150° C. for 6-18 h and calcined for 0.5-3 h, where the calcination temperature can be optimised with respect to the coating present in each case. In general, the calcination temperatures are between 500 and 1000° C., preferably between 600 and 900° C. If desired, the pigments can be separated off, dried and optionally calcined after application of individual coatings and then resuspended for precipitation of the further layers.

The precipitation of the $SiO_2$ layer on the substrate is generally carried out by addition of a potassium or sodium water-glass solution at a suitable pH.

The coating can furthermore also be carried out in a fluidised-bed reactor by gas-phase coating, it being possible to use correspondingly, for example, the methods proposed in EP 0 045 851 and EP 0 106 235 for the preparation of pearlescent pigments.

The hue of the pearlescent pigments can be varied in very broad limits through the different choice of the coating quantities or the layer thicknesses resulting therefrom. Fine tuning for a certain hue can be achieved beyond the pure choice of amount by approaching the desired colour under visual or measurement-technology control.

In order to increase the light, water and weather stability, it is frequently advisable to subject the finished pigment, depending on the area of use, to post-coating or post-treatment. Suitable post-coatings or post-treatments are, for example, the processes described in German Patent 22 15 191, DE-A 31 51 354, DE-A 32 35 017 or DE-A 33 34 598. This post-coating (layer D) further increases the chemical and photochemical stability or simplifies handling of the pigment, in particular incorporation into various media. In order to improve the wettability, dispersibility and/or compatibility with the user media, it is possible to apply, for example, functional coatings of $Al_2O_3$ or $ZrO_2$ or mixtures thereof to the pigment surface. Also possible are organic post-coatings, for example with silanes, as described, for example, in EP 0 090259, EP 0 634 459, WO 99/57204, WO 96/32446, WO 99/57204, U.S. Pat. No. 5,759,255, U.S. Pat. No. 5,571,851, WO 01/92425 or in J. J. Ponjeé, Philips Technical Review, Vol. 44, No. 3, 81 ff. and P. H. Harding J. C. Berg, J. Adhesion Sci. Technol. Vol. 11 No. 4, pp. 471-493.

The pigments according to the invention are compatible with a multiplicity of colour systems, preferably from the area of paints, coatings, printing inks and cosmetic formulations. A multiplicity of binders, in particular water-soluble products, as marketed, for example, by BASF, Marabu, Pröll, Sericol, Hartmann, Gebr. Schmidt, Sicpa, Aarberg, Siegberg, GSB-Wahl, Follmann, Ruco or Coates Screen INKS GmbH, is suitable for the preparation of printing inks, for example for gravure printing, flexographic printing, off-set printing and offset overprint varnishing. The printing inks can be water-based or solvent-based. Furthermore, the pigments are also suitable for the laser marking of paper and plastics and for applications in the agricultural sector, for example for greenhouse sheeting, and, for example, for the colouring of tarpaulins.

As a consequence of their increased chemical and mechanical stabilisation, the pearlescent pigments according to the invention are particularly suitable for polymers, in particular plastics. The plastics preferably comprise 0.01-10% by weight, in particular 0.3-5% by weight and very particularly preferably 0.5-2.5% by weight, of the pigments according to the invention. Even at pigment concentrations of 5% by weight, no significant dark yellowing of plastics comprising phenol-containing additives is evident. Furthermore, the pearlescent pigments are suitable for surface-coating formulations.

Since the pearlescent pigments according to the invention combine a particularly clear colour with intense interference colours and high brightness, particularly effective effects can be achieved with them in the various application media, for example in cosmetic formulations, such as nail varnishes, lipsticks, compact powders, gels, lotions, emulsions, soaps and toothpastes.

The pigments according to the invention may furthermore also be combined with cosmetic active ingredients. Suitable active ingredients are, for example, insect repellents, UV A/BC protective filters (for example OMC, B3, MBC), anti-ageing active ingredients, vitamins and derivatives thereof (for example vitamin A, C, E, etc.), self-tanning agents (for example DHA, erythrulose, inter alia) and further cosmetic active ingredients, such as, for example, bisabolol, LPO, ectoine, emblica, allantoin, bioflavonoids and derivatives thereof.

In self-tanning creams, lotions, sprays, etc., comprising, for example, the self-tanning agent DHA (dihydroxyacetone) and an effect pigment having a final $TiO_2$ layer, for example a glass flake coated with $TiO_2$ (anatase), the DHA is slowly degraded in the formulation. On use of the pigments according to the invention in the formulation, the action of the DHA is fully retained.

The formulations comprising the pearlescent pigments according to the invention can belong to the lipophilic, hydrophilic or hydrophobic type. In the case of heterogeneous formulations having discrete aqueous and non-aqueous phases, the pigments according to the invention may in each case be present in only one of the two phases or distributed over both phases.

It goes without saying that, for the various applications, the pearlescent pigments according to the invention can also advantageously be used as a blend with organic dyes, organic pigments or other pigments, such as, for example, transparent and opaque white, coloured and black pigments, and with flake-form iron oxides, organic pigments, holographic pigments, LCPs (liquid crystal polymers) and conventional transparent, coloured and black lustre pigments based on metal-oxide-coated mica and $SiO_2$ flakes, etc.

The pigments according to the invention can be mixed in any ratio with commercially available pigments and fillers.

Examples of fillers which may be mentioned are natural and synthetic mica, nylon powder, pure or filled melamine resins, talc, $SiO_2$, glasses, kaolin, oxides or hydroxides of aluminium, magnesium, calcium, zinc, BiOCl, barium sulfate, calcium sulfate, calcium carbonate, magnesium carbonate, carbon, and physical or chemical combinations of these substances.

There are no restrictions regarding the particle shape of the filler. It can be, for example, flake-form, spherical or needle-shaped as required.

The pigments according to the invention can of course also be combined in the formulations with any type of raw materials and auxiliaries. These include, inter alia, oils, fats, waxes, film formers, preservatives and auxiliaries which determine the technical properties in general, such as, for example, thickeners and rheological additives, such as, for example, bentonites, hectorites, silicon dioxides, Ca silicates, gelatins, high-molecular-weight carbohydrates and/or surface-active auxiliaries, etc.

The invention thus also relates to the use of the pearlescent pigments in formulations, such as paints, coatings, automobile paints, powder coatings, printing inks, security printing inks, plastics, ceramic materials, glasses, paper, in paper coating, in toners for electrophotographic printing processes, in seed, in greenhouse sheeting and tarpaulins, as absorbers in the laser marking of paper and plastics, as absorbers in the laser welding of plastics, cosmetic formulations, for the preparation of pigment pastes with water, organic and/or aqueous solvents, for the preparation of pigment compositions and dry preparations, such as, for example, granules.

The following examples are intended to explain the invention in greater detail, but without restricting it.

EXAMPLES

I. Preparation of the Pigments

Example 1

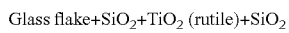
Glass flake+$SiO_2$+$TiO_2$ (rutile)+$SiO_2$ 150 g of glass flakes having an average layer thickness of 900 nm from the 20-200 μm fraction are heated to 75° C. with stirring in 1.9 l of deionised water. The pH of the suspension is then adjusted to 7.5 using a 5% hydrochloric acid. A sodium water-glass solution (112 g of sodium water-glass solution comprising 26.8% of $SiO_2$ dissolved in 112 g of deionised water) is subsequently added dropwise, during which the pH is kept constant at 7.5 by simultaneous metered addition of a 5% hydrochloric acid. When the addition is complete, the mixture is stirred for a further 0.5 h. The pH of the suspension is then adjusted to 1.8, the mixture is stirred for a further 15 minutes, and a solution of tin tetrachloride in hydrochloric acid (3 g of $SnCl_4*5 H_2O$ dissolved in 15 ml of 25% hydrochloric acid and 85 ml of deionised water) is added dropwise, during which the pH is kept constant by simultaneous dropwise addition of a 32% sodium hydroxide solution. When the addition is complete, the mixture is stirred for a further 15 minutes.

This is followed by metered addition of a 30% titanium tetrachloride solution, during which the pH is kept constant by simultaneous dropwise addition of a 32% sodium hydroxide solution. The colouristic properties are monitored during preparation of the pigment by measuring the colour during the process, and the precipitation process is controlled in accordance with the hue (hue angle arc tan b*/a*). When the desired silver end point has been reached, the mixture is stirred for a further 15 minutes.

The pH is adjusted to pH 9.0 using dilute sodium hydroxide solution. 100 ml of a sodium water-glass solution having a silicic acid content of 5% are added over the course of 2 hours, during which the pH is kept constant by means of 2.5% sulfuric acid. The mixture is subsequently stirred for a further 30 minutes, and the pH is then adjusted to 7.5 over the course of 30 minutes using sulfuric acid.

After the mixture has been stirred for a further 30 minutes, the post-coated pigment is separated off from the supernatant by filtration and washed. After drying at 100 to 150° C., the pigment is calcined at 700° C. for 45 minutes and sieved in accordance with the desired particle size.

The pigment obtained in this way comprises a coating of silicon dioxide having a layer thickness of about 18-28 nm.

Example 2A

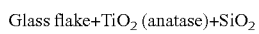
Glass flake+$TiO_2$ (anatase)+$SiO_2$ 150 g of glass flakes having an average layer thickness of 900 nm from the 20-200 μm fraction are heated to 75° C. with stirring in 1.9 l of deionised water. The pH of the suspension is then adjusted to 2.0 using conc. hydrochloric acid.

This is followed by metered addition of a 30% titanium tetrachloride solution, during which the pH is kept constant by simultaneous dropwise addition of a 32% sodium hydroxide solution. The colouristic properties are monitored during preparation of the pigment by measuring the colour during the process, and the precipitation process is controlled in accordance with the hue (hue angle arc tan $b^*/a^*$). When the desired silver end point has been reached, the mixture is stirred for a further 15 minutes.

The pH is adjusted to pH 9.0 using dilute sodium hydroxide solution. 100 ml of a sodium water-glass solution having a silicic acid content of 5% are added over the course of 2 hours, during which the pH is kept constant by means of 2.5% sulfuric acid. The mixture is subsequently stirred for a further 30 minutes, and the pH is then adjusted to 7.5 over the course of 30 minutes using sulfuric acid.

After the mixture has been stirred for a further 30 minutes, the post-coated pigment is separated off from the supernatant by filtration and washed. After drying at 100 to 150° C., the pigment is calcined at 700° C. for 45 minutes.

The pigment obtained in this way comprises a coating of silicon dioxide having a layer thickness of about 18-28 nm.

Example 2B

Glass flake+$TiO_2$ (rutile)+$SiO_2$ 150 g of glass flakes having an average layer thickness of 900 nm from the 20-200 µm fraction are heated to 75° C. with stirring in 1.9 l of deionised water. The pH of the suspension is then adjusted to 2.0, the mixture is stirred for a further 15 minutes, and a solution of tin tetrachloride in hydrochloric acid (3 g of $SnCl_4*5$ $H_2O$ dissolved in 15 ml of 25% hydrochloric acid and 85 ml of deionised water) is added dropwise, during which the pH is kept constant by simultaneous dropwise addition of a 32% sodium hydroxide solution. When the addition is complete, the mixture is stirred for a further 15 minutes.

This is followed by metered addition of a 30% titanium tetrachloride solution, during which the pH is kept constant by simultaneous dropwise addition of a 32% sodium hydroxide solution. The colouristic properties are monitored during preparation of the pigment by measuring the colour during the process, and the precipitation process is controlled in accordance with the hue (hue angle arc tan $b^*/a^*$). When the desired silver end point has been reached, the mixture is stirred for a further 15 minutes.

The pH is adjusted to pH 9.0 using dilute sodium hydroxide solution. 100 ml of a sodium water-glass solution having a silicic acid content of 5% are added over the course of 2 hours, during which the pH is kept constant by means of 2.5% sulfuric acid. The mixture is subsequently stirred for a further 30 minutes, and the pH is then adjusted to 7.5 over the course of 30 minutes using sulfuric acid.

After the mixture has been stirred for a further 30 minutes, the post-coated pigment is separated off from the supernatant by filtration and washed. After drying at 100 to 150° C., the pigment is calcined at 700° C. for 45 minutes.

The pigment obtained in this way comprises a coating of silicon dioxide having a layer thickness of about 18-28 nm.

Example 3

Glass flake+$TiO_2$+$Al_2O_3$ 150 g of glass flakes having an average layer thickness of 900 nm from the 20-200 µm fraction are heated to 75° C. with stirring in 1.9 l of deionised water. The pH of the suspension is then adjusted to 2.0 using conc. hydrochloric acid.

This is followed by metered addition of a 30% titanium tetrachloride solution, during which the pH is kept constant by simultaneous dropwise addition of a 32% sodium hydroxide solution. The colouristic properties are monitored during preparation of the pigment by measuring the colour during the process, and the precipitation process is controlled in accordance with the hue (hue angle arc tan $b^*/a^*$). When the desired silver end point has been reached, the mixture is stirred for a further 15 minutes.

The pigment suspension obtained is adjusted to pH 6.5 using 32% NaOH. After the mixture has been stirred for 15 minutes, 5.33 g of $AlCl_3 \times 6$ $H_2O$ and 3.20 g of sodium sulfate in solid form are added. The suspension obtained is stirred at 90° C. for 1 h. The aqueous solution is subsequently filtered with suction and washed until chloride-free, and the product is dried. The product is calcined at 700° C. for 30 minutes.

Example 4

Glass flake+$TiO_2$+5% $SiO_2$/2.5% $Al_2O_3$ (2:1)

150 g of glass flakes having an average layer thickness of 900 nm are heated to 75° C. with stirring in 1.9 l of deionised water. The pH of the suspension is then adjusted to 2.0 using conc. hydrochloric acid.

This is followed by metered addition of a 30% titanium tetrachloride solution, during which the pH is kept constant by simultaneous dropwise addition of a 32% sodium hydroxide solution. The colouristic properties are monitored during preparation of the pigment by measuring the colour during the process, and the precipitation process is controlled in accordance with the hue (hue angle arc tan $b^*/a^*$). When the desired silver end point has been reached, the mixture is stirred for a further 15 minutes.

The pigment suspension obtained is adjusted to pH 9 using 32% NaOH. After addition of the sodium water-glass solution (diluted with water in the ratio 1:1; 39 ml in 1000 ml of water), the mixture is stirred for 15 minutes, and the pH is adjusted to pH 6.5 using conc. HCl. After the mixture has been stirred for 15 minutes, 5.33 g of $AlCl_3 \times 6$ $H_2O$ and 3.20 g of sodium sulfate in solid form are added. The suspension obtained is stirred at 90° C. for 1 h. The aqueous solution is subsequently filtered with suction and washed until chloride-free, and the product is dried. The product is calcined at 700° C. for 30 minutes.

Example 5

Glass flake+$TiO_2$+$SiO_2$ (doped with $K^+$)

150 g of glass flakes having an average layer thickness of 900 nm from the 20-200 µm fraction are heated to 75° C. with stirring in 1.9 l of deionised water. The pH of the suspension is then adjusted to 2.0 using conc. hydrochloric acid.

This is followed by metered addition of a 30% titanium tetrachloride solution, during which the pH is kept constant by simultaneous dropwise addition of a conc. potassium hydroxide solution. The colouristic properties are monitored during preparation of the pigment by measuring the colour during the process, and the precipitation process is controlled in accordance with the hue (hue angle arc tan $b^*/a^*$). When the desired silver end point has been reached, the mixture is stirred for a further 15 minutes.

The pH is adjusted to pH 9.0 using dilute potassium hydroxide solution. 100 ml of a potassium water-glass solution having a silicic acid content of 5% are added over the course of 2 hours, during which the pH is kept constant by means of 2.5% sulfuric acid. The mixture is subsequently stirred for a further 30 minutes, and the pH is then adjusted to 7.5 over the course of 30 minutes using sulfuric acid.

After the mixture has been stirred for a further 30 minutes, the post-coated pigment is separated off from the supernatant by filtration and washed.

After drying at 100 to 150° C., the pigment is calcined at 700° C. for 45 minutes. The pigment obtained in this way comprises a coating of silicon dioxide having a layer thickness of about 18-28 nm.

Example 6

Comparative Example of a Pigment Which Exhibits Yellowing glass flake+$TiO_2$ (rutile)

150 g of glass flakes having an average layer thickness of 900 nm from the 20-200 µm fraction are heated to 75° C. with stirring in 1.9 l of deionised water. The pH of the suspension is then adjusted to 2.0, the mixture is stirred for a further 15 minutes, and a solution of tin tetrachloride in hydrochloric acid (3 g of $SnCl_4*5 H_2O$ dissolved in 15 ml of 25% hydrochloric acid and 85 ml of deionised water) is added dropwise, during which the pH is kept constant by simultaneous dropwise addition of a 32% sodium hydroxide solution. When the addition is complete, the mixture is stirred for a further 15 minutes.

This is followed by metered addition of a 30% titanium tetrachloride solution, during which the pH is kept constant by simultaneous dropwise addition of a 32% sodium hydroxide solution. The colouristic properties are monitored during preparation of the pigment by measuring the colour during the process, and the precipitation process is controlled in accordance with the hue (hue angle arc tan b*/a*). When the desired silver end point has been reached, the mixture is stirred for a further 15 minutes.

After the mixture has been stirred for a further 30 minutes, the post-coated pigment is separated off from the supernatant by filtration and washed.

After drying at 100 to 150° C., the pigment is calcined at 700° C. for 45 minutes.

II. Stability Investigations 2.1 Yellowing (Plastic)

The phenomenon of "yellowing" is not simple to describe in chemical terms. The effect is observed, inter alia, on use of $TiO_2$-containing pigments, which form yellowish complexes together with phenolic substances, depending on their structure, under various ambient influences. The result of "yellowing" is the change in the colour of the sample towards yellow. Since the colour changes to a yellow hue, it is best to use the b value for colorimetric description of "yellowing" in the Lab system.

In thermoplastics, this yellowing is observed in the following colourings in Example 7, while Example 8 shows the state according to the invention without yellowing. The yellowing is of course particularly striking in the case of very pale or silver-white colours.

Example 7

1.6 kg of PE-LLD powder (Escorene 6101 RQ from Exxon) are mixed for 10 minutes with 400 g of pigment according to Example 6 in a suitable mixer and subsequently melted in a twin-screw extruder, mixed and converted into masterbatch granules having a silvery lustre via a granulation device.

This masterbatch changes its silvery white colour significantly to yellow on the side facing the light on storage in a moderately brightly illuminated storeroom over the course of two weeks. Assessed in accordance with the grey scale (DIN EN 20105-A02), an assessment of 2 G (yellow) is obtained.

Example 8

1.6 kg of PE-LLD powder (Escorene 6101 RQ from Exxon) are mixed for 10 minutes with 400 g of a pigment according to the invention (prepared in accordance with Example 2B) in a suitable mixer and subsequently melted in a twin-screw extruder, mixed and converted into masterbatch granules having a silvery lustre via a granulation device.

This masterbatch does not change its silvery white colour on storage in a moderately brightly illuminated storeroom over the course of two weeks. Assessed in accordance with the grey scale (DIN EN 20105-A02), an assessment of 5 is obtained, i.e. no change in colour.

2.2 Quantitative Determination of Yellowing

With the aid of the following method, the yellowing can be determined quantitatively:

0.1 g of the sample to be tested is introduced into a measurement cell. 0.4 ml of a solution consisting of 5% of propanol/95% of dibutyl phthalate is added. The suspension is shaken for one minute, and the b value is subsequently measured using a Minolta CR 300 calorimeter. The b value is determined at an angle of 45°/0.0.5 ml of a propyl galate (propyl 3,4,5-trihydroxybenzoate) solution (10% in 40% of propanol/60% of dibutyl phthalate) is subsequently added. The suspension is shaken for 3 minutes and subsequently left to stand for 1 minute. The b value is re-measured, and the difference in the b value between the first and second measurements is determined. The yellowing is obtained from the change in the b value.

Example 9 a) Sample according to Example 6 shows yellowing: delta b value of +4.5 b) Sample according to Example 2B shows no yellowing: delta b value of +0.1

2.3 Stability Investigation 10 g of pearlescent pigment are in each case suspended in 100 ml of water and stressed mechanically by rapid stirring.

The results of the mechanical stability investigation with respect to size and fraction distribution of the pigments are shown below in Table 1:

TABLE 1

|  | Unstressed $D_{50}$ | Stressed $D_{50}$ | Unstressed $D_{95}$ | Stressed $D_{95}$ |
| --- | --- | --- | --- | --- |
| Pigment according to Example 6 (comparison) | 82 | 71 | 188 | 147 |
| Pigment according to Example 2B (according to the invention) | 82 | 82 | 179 | 179 |

USE EXAMPLES

Use Example 1

Self-Tanning Care Cream (O/W)

| Ingredients | | INCI | [%] |
|---|---|---|---|
| Phase A | | | |
| Montanov 68 | (1) | Cetearyl Alcohol, Cetearyl Glucoside | 4.00 |
| Span 60 | (2) | Sorbitan Stearate | 1.50 |
| Lanette O | (3) | Cetearyl Alcohol | 1.00 |
| Cosmacol ELI | (4) | C12-13 Alkyl Lactate | 3.00 |
| Cosmacol EMI | (4) | DI-C12-13 Alkyl Malate | 1.50 |
| Arlamol HD | (2) | Isohexadecane | 3.00 |
| Dow Corning 9040 Silicone Elastomer Blend | (5) | Cyclomethicone, Dimethicone Crosspolymer | 1.00 |
| RonaCare ® Tocopherol Acetate | (6) | Tocopheryl Acetate | 0.50 |
| Propyl 4-hydroxybenzoate | (6) | Propylparaben | 0.05 |
| Phase B | | | |
| RonaCare ® Ectoin | (6) | Ectoin | 0.50 |
| Pigment according to Example 1 or Example 2 | | | 2.00 |
| Glycerol, anhydrous | (6) | Glycerin | 2.00 |
| FD&C Yellow No. 6 W082 | (8) | CI 15985 | 0.01 |
| Methyl 4-hydroxybenzoate | (6) | Methylparaben | 0.15 |
| Water, demineralised | | Aqua (Water) | 64.69 |
| Phase C | | | |
| Sepigel 305 | (1) | Laureth-7, Polyacrylamide, C13-14 Isoparaffin | 0.50 |
| Phase D | | | |
| Dihydroxyacetone | (6) | Dihydroxyacetone | 5.00 |
| Water, demineralised | | Aqua (Water) | 10.00 |
| Phase E | | | |
| Fragrance Babylon | (9) | Parfum | 0.20 |

Preparation:

Phases A and B are warmed separately to 75° C. Phase B is then slowly admixed with phase A with stirring. Phase C is admixed and homogenised with phases A/B at 60° C. using a hand stirrer. Allow to cool to 40° C., and stir in phase D and phase E.

Notes:

pH (23° C.)=4.0

Viscosity: 18,600 cps (Brookfield model RVT DV-II, Helipath spindle C, 10 rpm) at 23° C.

Sources of Supply:
(1) Seppic
(2) Uniqema
(3) Cognis GmbH f;
(4) Condea Chimica D.A.C. S.p.A.
(5) Dow Corning
(6) Merck KGaA/Rona®
(7) D.D. Williamson
(8) Les Colorants Wackherr SA
(9) Drom

Use Example 2

Self-Tanning Cream (O/W)

| Ingredients | | INCI | [%] |
|---|---|---|---|
| Phase A | | | |
| Tego Care 150 | (1) | Glyceryl Stearate, Steareth-25, Ceteth-20, Stearyl Alcohol | 8.00 |
| Paraffin, liquid | (2) | Parffinum Liquidum (Mineral Oil) | 12.00 |
| Paraffin, pourable | (2) | Paraffin | 2.00 |
| Miglyol 812 N | (3) | Caprylic/Capric Triglyceride | 3.00 |
| Isopropyl myristate | (4) | Isopropyl Myristate | 2.00 |
| Propyl 4-hydroxybenzoate | (2) | Propylparaben | 0.15 |
| Phase B | | | |
| 1,2-Propanediol | (2) | Propylene Glycol | 4.00 |
| Sorbitol F liquid | (2) | Sorbitol | 2.00 |
| Water, demineralised | | Aqua (Water) | 47.40 |
| Methyl 4-hydroxybenzoate | (2) | Methylparaben | 0.15 |
| Pigment according to Example 1 or Example 2 | | | 2.00 |
| Phase C | | | |
| Dihydroxyacetone | (2) | Dihydroxyacetone | 5.00 |
| Water, demineralised | | Aqua (Water) | 11.80 |
| Phase D | | | |
| Fragrance (q.s.) | | Parfum | 0.50 |

Preparation:

Phase A is warmed to 80° C. and phase B to 75° C. Phase A is then slowly added to phase B with stirring. The mixture is homogenised for one minute at 65° C. using a hand stirrer. Allow to cool to 40° C. and stir in phase C. Cool further to 35° C. and stir in phase D.

Notes:

pH (23° C.)=4.6

Viscosity: 42,500 mPas (Brookfield RVT, spindle C, 10 rpm) at 23° C.

Sources of Supply:
(1) Degussa-Goldschmidt AG
(2) Merck KGaA/Rona®
(3) Sasol Germany GmbH
(4) Cognis GmbH

The invention claimed is:

1. Pearlescent pigments consisting of glass flakes; and on the surface of the glass flake a layer sequence consisting of
    (A) a layer of $SiO_2$, which is optionally full or partially coated with $SnO_2$ or $SnO_2$ nuclei,
    (B) a high-refractive-index coating having a refractive index n>1.8 which essentially consists of $TiO_2$,
    (C) a low-refractive-index layer of $SiO_2$ and/or $Al_2O_3$, having a refractive index n<1.8 and optionally doped with one or more oxides of V, Zr, Zn, Ce, Ti, B, Na, K, Mg, Ca and/or Mn
    and optionally
    (D) an outer silane protective layer.

2. Pearlescent pigments according to claim 1, wherein layer (A) has a thickness of 2-350 nm.

3. Pearlescent pigments according to claim 1, wherein layer (B) has a thickness of 20-300 nm.

4. Pearlescent pigments according to claim 1, wherein layer (C) has a thickness of 2-200 nm.

5. Pearlescent pigments according to claim 1, wherein (C) is doped with one or more oxides of V, Zr, Zn, Ce, Ti, B, Na, K, Mg, Ca and/or Mn.

6. Pearlescent pigments according to claim 1, wherein the $TiO_2$ in layer (B) is in rutile modification.

7. Pearlescent pigments according to claim 6, wherein layer (A) of $SnO_2$ or $SnO_2$ nuclei is present.

8. Pearlescent pigments according to claim 1, having one of the following layer structures:

glass flake+$SiO_2$+$TiO_2$+$SiO_2$ glass flake+$SiO_2$+$TiO_2$+$SiO_2$/$Al_2O_3$ glass flake+$SiO_2$+$TiO_2$+Al2O3.

9. Pearlescent pigments according to claim 1, having an outer protective layer (D) increasing light, temperature and weather stability.

10. Process for the preparation of the pearlescent pigments according to claim 1, comprising coating of the glass flakes by wet-chemical methods, by hydrolytic decomposition of metal salts in aqueous medium, or in a fluidized-bed reactor by gas-phase coating.

11. Paints, coatings, automobile paints, powder coatings, printing inks, security printing inks, plastics, ceramic materials, glasses, paper, toners for electrophotographic printing processes, seed, greenhouse sheeting or tarpaulins, absorbers in laser marking of paper and plastics, absorbers in laser welding of plastics, cosmetic formulations, pigment pastes with water, organic and/or aqueous solvents, or dry pigment preparations, comprising a pigment according to claim 1.

12. A method for inhibiting yellowing of polymers containing phenolic additives, comprising adding thereto a pigment according to claim 1.

13. Cosmetic formulations comprising dihydroxyacetone and a pigment according to claim 1.

* * * * *